United States Patent [19]

Schwan

[11] 4,048,176
[45] Sept. 13, 1977

[54] 2-(3-METHYL-4-PHENYL-1,2,3,4-TETRAHYDRO-2-ISOQUINOLYL)-ACETAMIDOXIME DIHYDROCHLORIDE

[75] Inventor: Thomas J. Schwan, Norwich, N.Y.

[73] Assignee: Morton-Norwich Products, Inc., Norwich, N.Y.

[21] Appl. No.: 708,066

[22] Filed: July 23, 1976

[51] Int. Cl.² .......................................... C07D 217/04
[52] U.S. Cl. ........................ 260/286 R; 260/288 D; 260/283 CN; 260/283 SY; 424/258
[58] Field of Search ....... 260/286 R, 288 D, 283 CN, 260/283 SY

[56] References Cited

U.S. PATENT DOCUMENTS

| | | | |
|---|---|---|---|
| 3,517,015 | 6/1970 | Ott | 260/283 CN |
| 3,673,188 | 6/1972 | Harsanyi et al. | 260/288 D |
| 3,686,184 | 8/1972 | Bailey | 260/288 D |

*Primary Examiner*—Paul M. Coughlan, Jr.
*Attorney, Agent, or Firm*—Anthony J. Franze

[57] ABSTRACT

A compound 2-(3-methyl-4-phenyl-1,2,3,4-tetrahydro-2-isoquinolyl) acetamidoxime dihydrochloride possesses pharmacological activity as an antidepressant.

1 Claim, No Drawings

2-(3-METHYL-4-PHENYL-1,2,3,4-TETRAHYDRO-2-ISOQUINOLYL)-ACETAMIDOXIME DIHYDROCHLORIDE

This invention relates to a chemical compound. In particular it is concerned with a compound of the formula:

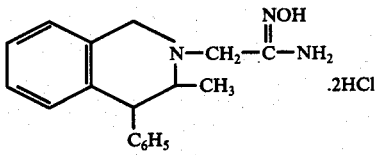

This compound possesses pharmacological activity affecting the central nervous system. When administered perorally to animals it exhibits anti-despressant action. Its antidepressant property is evidenced in the control to tetrabenazine-induced ptosis in mice. An oral dose of 50 mg/kg of this compound to mice intraperintoneally receiving 35 mg/kg of tetrabenazine counteracts the ptosis producing property of tetranbenazine.

In order that this invenion be readily available to and understood by those skilled in the art the following illustration is included:

A.
2-Cyanomethyl-3-methyl-4-phenyl-1,2,3,4-tetrahydroisoquinoline

A suspension of 3-methyl-4-phenyl-1,2,3,4-tetrahydroisoquinoline hydrobromide (121 g, 0.4 mole), potassium carbonate (110 g, 0.8 mole), and chloroacentonitrile (30 g, 0.4 mole) in 750 ml ethanol was reluxed for 24 hours. The mixture was filtered, the filtrate collected and concentrated to dryness in vacuo. The oil was partitioned between 250 ml mchloroform and 250 ml water. The chloroform was dried (MgSP$_4$) and concentrated to dryness. This oil was crystallized from hexane to yield 79 gms (75%) of A.

An analytical sample, m.p. 106.5°–110°, was recrystallized twice from hexane.

Anal. Calcd. for $C_{18}H_{18}N_2$: C, 82.41; H, 6.91; N, 10.68.

Found: C, 82.50; H, 6.93; N, 10.72.

B.
2-(3-Methyl-4-phenyl-1,2,3,4-tetrahydro-2-isoquinolyl)acetamidoxime
Dihydrochloride A suspension of A (44 g, 0.17 mole) in 400 ml methanol was treated with hydroxylamine hydrochloride and then cooled to 0°. To the cooled suspension was added a methanolic solution of sodium methylate (9.2 g, 0.17 mole) in small portions at 0°–5°. The reaction mixture was allowed to gradually raise to ambient temperature over a period of 24 hrs. After removing the solvent in vacuo the residue was partitioned between 200 ml chloroform and 200 ml water. The aqueous layer was washed with chloroform (200 ml) and then discarded. The chloroform extracts were combined, washed with water (200 ml), dried (MgSo$_4$), and concentrated to dryness leaving 38 gms (79%) of the free base.

The hydrochloride was prepared by suspending the free base (38 g) in methanol (500 ml) and treating with methanolic hydrogen chloride. The alcoholic solution was concentrated to dryness in vacuo and the residue was crystallized from ethanol-ethyl acetate to give 35 g (56% overall) of the product.

An analytical sample, m.p. 188°–190°, was recrystalized from isopropanol.

Anal. Calcd. for $C_{18}H_{21}N_3O·2HCl$: C, 58.70; H, 6.29; N, 11.41. Found: C, 58.57; H, 6.28; N, 11.42.

What is claimed is:
1. A compound of the formula:

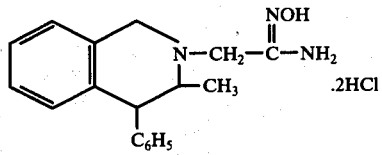

* * * * *